United States Patent [19]

Bowers

[11] 4,007,262
[45] Feb. 8, 1977

[54] ODOR CONTROL COMPOSITIONS FOR USE IN CHEMICAL TOILET SYSTEMS

[76] Inventor: Wayne E. Bowers, P.O. Box 615, Stanhope, N.J. 07874

[22] Filed: Apr. 5, 1973

[21] Appl. No.: 348,150

[52] U.S. Cl. .................................... 424/76
[51] Int. Cl.² .................................. A61L 13/00
[58] Field of Search .......................... 424/76

[56] References Cited

UNITED STATES PATENTS

| | | | |
|---|---|---|---|
| 1,063,313 | 6/1913 | Anders | 424/76 X |
| 3,107,216 | 10/1963 | Hamilton | 210/60 |
| 3,124,460 | 3/1964 | Erwin | 424/76 X |
| 3,198,251 | 8/1965 | Shore | 424/76 |
| 3,208,936 | 9/1965 | Hamilton | 424/76 X |
| 3,314,745 | 4/1967 | Krotinger et al. | 210/59 X |
| 3,317,372 | 5/1967 | Hart | 424/76 |
| 3,509,254 | 4/1970 | Krotinger, Jr. et al. | 424/76 |
| 3,556,949 | 1/1971 | Putnam et al. | 203/6 |

FOREIGN PATENTS OR APPLICATIONS 413,939   7/1934   United Kingdom

Primary Examiner—Albert T. Meyers
Assistant Examiner—Allen J. Robinson
Attorney, Agent, or Firm—Ernest V. Haines

[57] ABSTRACT

An odor control composition principally for use in closed recirculating and holding tank type chemical toilet systems comprises at least one substantially neutral or basic transition metal salt of an inorganic acid or a lower aliphatic organic monocarboxylic acid dissolved in aqueous ammonia or an aqueous solution of a strong water soluble organic amine which is subsequently acidified with sufficient mono- or polyfunctional carboxylic acid or other suitable acidic ligand to produce a transition metal coordination compound and a buffer system in aqueous solution, whose pH is at least about 6.5 and preferably is at least about 7.0. The composition may, optionally also contain, an inorganic oxidizing agent such as an alkali metal nitrate, alkali metal permanganate, or alkali metal chlorite, a wetting or emulsifying organic sulfonate or sulfate, and for esthetic purposes, a masking agent such as a fragrance and a neutral or alkaline stable dye.

9 Claims, No Drawings

ODOR CONTROL COMPOSITIONS FOR USE IN CHEMICAL TOILET SYSTEMS

DESCRIPTION OF THE INVENTION

The present invention relates to the preparation and use of novel odor control compositions in chemical, sanitary, self-contained, recirculating or non-recirculating toilets such as those used in busses, airplanes, boats, mobile homes, cabins, construction sites, etc. or in any other instances where permanent sewerage facilities are unavailable. In such instances, i.e. a lack of ready connection or access to permanent type sewerage systems or by the very nature of the requirements of mobility, it is necessary to still provide satisfactory methods of holding and/or disposing of fecal wastes until they may be discharged into suitable waste treatment and disposal facilities of a permanent type. Until such ultimate disposal, however, such urinary and fecal wastes must be accommodated as innocuously as possible and such temporary treatment thereof must not interfere with their subsequent efficacious treatment in more complete permanent treatment plants.

The novel compositions hereinafter described are added to the liquid system of chemical toilets (both holding tank and recirculating tank systems) for the purpose of controlling odors, chiefly through chemical reactions, in contrast to the use of a masking agent, although such agents may be used optionally to some degree. In the past, this problem has been attempted to be solved through the use, in an aqueous system, of a water soluble zinc salt such as zinc chloride, zinc nitrate, zinc sulfate or zinc acetate and optionally in the presence of sodium nitrate as an oxidizing agent. (See U.S. Pat. No. 3,314,745). However, it has been found that free zinc ion is rapidly exhausted when wastes are added to the system. U.S. Pat. No. 3,107,216 teaches that heretofore, for the same purposes, phenols, cresols, caustic soda, lime, chlorohydrocarbons, pine oil disinfectants, quaternary ammonium salts or soaps, germicides, perfumes and emulsifying agents, inter alia, have been used but with varying degrees of success. Shore, U.S. Pat. No. 3,198,251 shows a combination of an alkali metal nitrite with a benzethonium quaternary salt such as a chloride and, optionally, an alkali metal bicarbonate may be similarly used. U.S. Pat. No. 3,556,949 shows the use of hexavalent chromium in the form of ammonium chromate, formed in situ, in urine to be effective for extracting potable water from urine by distillation. The chromium ion is added, however, in a solution of sulfuric acid and the treatment specifies that the pH should be at least 2, up to 7.0, preferably between 2 and 5 during treatment. U.S. Pat. No. 3,208,936 for the purpose of controlling odors, corrosion, destroying bacteria, etc. provides a foamy composition of an imidazolinium halide, an imidazoline, a quaternary amine, isopropanol, isopropanol solution of soya trimethylammonium chloride, either acetic or lactic acid, and formaldehyde. Finally, U.S. Pat. No. 3,509,254, issued to Krotanger et al, employs a composition, for recirculating and non-recirculating chemical toilets, of an inorganic zinc salt in combination with a chelating organic mono- or di-carboxylic acid. An acid hydrogen ion (pH) concentration was maintained which would eventually give rise to metal corrosion problems in the systems and the absence of buffering results in rapid exhaustion of the metal as wastes are added to the essentially acidic medium.

The novel compositions herein described are used as aqueous solutions, essentially neutral or basic in character. Since they are buffered by buffering agents which are formed in situ by the addition of the reactants necessary to form such agents, the pH of the novel aqueous liquid compositions may range from about 6.5 up to 11 but it is preferably between about 7.0 and about 10.5.

The novel liquid compositions are formaldehyde-free, ones whose basic ingredient is at least one transition metal salt (the metal being from Groups IB, IIB, IVB, VIB, VIIB and VIII of the Periodic Table), the metal of which is capable of forming an ammonia complex (ammine) or metal-amine complex of the salts. The preferred metals are copper, nickel, manganese, chromium, zinc, and zirconium. The anions are generally those of the strong acids such as chloride, nitrate, sulfate, bromide, trichloroacetate, etc., although acetate, formate, citrate, etc. could also be used. The salts, however, are limited to those which are water soluble or are rendered water soluble when added to the ammonia or amine aqueous solution. Mixtures of two or more of these suitable salts of different metals may be employed and the same transition metal may be used in the form of two or more salts (i.e. two or more different anions). Typical transition metal salts, in their non-complex form, are zinc chloride, zinc sulfate, zinc nitrate, zinc acetate, zinc bromide, cupric chloride or bromide, cupric sulfate, cupric nitrate, cupric acetate, the nickel, manganese and chromium corresponding salts of the same anions as well as the chlorides, bromides, nitrates, sulfates, acetates and trichloroacetates of the other transition metals mentioned above, provided they form water soluble ammonia or amine complexes. The metals, as above set forth, are desirably in combination with one or more of the anions above stated in their highest oxidation (stable) state in view of the fact that oxidizing agents such as potassium permanganate, sodium nitrate, potassium chlorite, ammonium persulfate and the like are optionally present in the final compositions. If and when the metal salts are added wherein the valence of the metal is in a reduced state, the use of additional amounts of oxidizing agents may be required for the additional purpose of converting the metals in the salts to their fully oxidized (stabile) state.

In addition to the metal salts being used and for the purpose of solubilizing and complexing said metal salts in the aqueous liquid composition, a second essential component, i.e. sufficient aqueous ammonia or amine is added. In many instances, especially during the compounding operation, enough aqueous ammonia or amine is added to maintain the pH above 10.5, preferably about 11.0, in order to prevent the precipitation of the metal salts therein. Although aqueous ammonia is the preferred complexing agent, it was found that other organic-substituted ammonia compounds such as water soluble primary, secondary or tertiary amines such as, dimethyl ethanol amine, monoethanolamine, triethanolamine, diethylene triamine, etc. are useful equivalents to ammonia especially in those instances where the metal used (e.g. manganese) does not form a stable coordination compound (complex) with ammonia alone. Although it is believed that eventually the hydroxyl concentration of the aqueous solution of metal complexes results in the conversion of the metals added to insoluble metal hydroxides which are thought to be the actual effective and long lasting agents in minimizing urinary and fecal odors, there is no intention of being bound to any theory as to why or how the use of the novel aqueous composition for the intended purpose, accomplishes the efficacious results attained. Suffice it to say that the novel aqueous composition when used in closed circuit toilets results in advantageous results over periods of time, without replacement or addition, of from 10 to 20 times longer duration than has heretofore been attained.

A third essential ingredient of the novel aqueous composition provides for the generation into the mixture of a buffer system, in situ. This is added to insure the presence and maintainence of hydroxyl ions in the toilet system. A weak lower alkyl or lower alkylene or phenylene organic mono- or polyfunctional carboxylic acid or anhydride thereof is employed for this purpose. Suitable acids include, for example, the following acids: citric, formic, acetic, propionic, butyric, phthalic, oxalic, malonic, benzoic, succinic, glutaric, adipic and the anhydrides thereof.

The use of such acids is limited to ones which form water soluble salts with the particular metal(s) chosen; otherwise complete destruction of the complex and precipitation of the insoluble metal carboxylate will occur.

Some proton donating compounds that fall outside the above classification are also useful. Examples are ammonium bicarbonate, sodium bisulfate and sulfamic acid.

The relative amounts of transition metal salts, and carboxylic acids may vary considerably. Based on their weight percentage amounts in water, these may vary, for example, between about 2% and about 30% of metal salt, preferably between about 15% and about 25%. The amount of weak carboxylic acid buffer component may vary between about 1% and about 20%, preferably between about 10% and about 15%. It is, of course, readily recognized that the amount of ammonium hydroxide added as 28% $NH_4OH$, or other commercial concentration, is sufficient to maintain a pH of at least 10.5 during compounding and ultimately enough ammonia or amine is added to form the stoichiometric complex of the metal employed. The amount of carboxylic acid or anhydride added is sufficient only to lower the pH generally to about 7.0 to 8.0. The following general equations illustrate formation of the novel composition.

Reaction I

Dissolution of the transition metal in aqueous ammonia to form the complex:

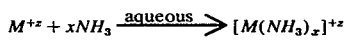

where
$M$ = transition metal having a valence $+z$.
$x$ = positive integer from 1–6.

Reaction II

Acidification of the complex ion and generation of the buffer system:

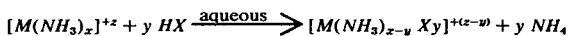

where $HX$ = the acid
$y$ = Any positive number less than 6 and equal to or less than $z$.

The process of formulating the novel aqueous liquid deodorizing and stabilizing compositions for use in closed system chemical toilets may be carried out in the following manner: Dilute aqueous ammonia solution of pH greater than 11.0 has added thereto, with stirring, the water soluble solid transition metal salt or mixture of metal salts, or first one such metal salt is added, the pH adjusted with ammonia or amine back up to a pH greater than 10.5 followed by the addition of a second such metal salt, with the pH, if necessary, again being similarly adjusted upward to a pH of greater than 10.5. The pH adjustment or adjustments are accomplished by the admixing into the solution of additional quantities of ammonium hydroxide, usually as 28% $NH_4OH$ or some other convenient concentration of $NH_4OH$ or by using a suitable water soluble amine. While adding the said metal salt or salts, sufficient ammonia should be added if the pH falls to 10.5 or below in order to avoid the precipitation of reagents and to clear up any cloudiness that is observed during the salt dissolution. In all, enough ammonia or amine to form the stoichiometric coordination complex is added to obtain complete solubility. If an oxidizing agent is to be added, such as sodium nitrate, this material is then added slowly with stirring, until it is dissolved.

Thereafter, the solution is acidified with a weak organic mono- or polyfunctional carboxylic acid or anhydride thereof added in sufficient amount to obtain a pH of from about 6.5 to about 8.0, preferably about 7.0 to 8.0 in the composition.

Optionally, various emulsifying agents, compatible with a neutral or slightly basic aqueous medium, a fragrance, usually in an organic solvent or essential oil vehicle, and/or a suitable dyestuff also stable in the said aqueous medium, may be added, as desired. It is not necessary to add these three last mentioned materials in order to successfully accomplish the purpose for which the aqueous composition is intended, i.e. the deodorizing and control of closed system chemical toilets during their usage. One or more of these materials are generally added for esthetic purposes only, although the use of a suitable emulsifier does aid in solubilizing and distributing an added fragrance material which is usually sold and received, in commerce, in a suitable essential oil or organic solvent vehicle. The emulsifier also serves, during the usage of the composition in chemical toilet systems, as an aid in keeping any water insoluble metal hydroxides formed, in situ, or insoluble by products from caking in the system.

The following examples will serve to illustrate the more specific nature of the invention.

EXAMPLE 1

1000 lbs. of water has added thereto 1200 lbs. of 26° Be. ammonium hydroxide. 550 lbs. of zinc sulfate monohydrate is then slowly added, with stirring, to the dilute ammonium hydroxide. Thereafter, in like manner, 200 lbs. of zinc nitrate is added thereto, and then 200 lbs. of sodium nitrate was dissolved therein. The solution then is brought to a pH of 7.0–7.5 by the addition of 450 lbs. of acetic acid (99% conc.) after which 10 lbs. of an alkaline stable water soluble emulsifier, 8 lbs. of a blue dyestuff, and 10 lbs. of a commercially available fragrance were stirred in.

This material was added to a chemical toilet closed system in the ratio of one pint of the above composition per 2.5 gallons of water in the system. It was left in usage for a total of 61 days until the system was filled to capacity at which time the system was closed down. No odor problem was encountered during the entire 61 days.

EXAMPLE 2

1000 lbs. of water has added thereto 1200 lbs. of 26° Be. ammonium hydroxide. 550 lbs. of anhydrous zinc acetate is then slowly added, with stirring, to the dilute ammonium hydroxide. Thereafter in a like manner, 200 lbs. of zinc nitrate is added thereto and then 200 lbs. of sodium nitrate was dissolved therein. The solution then is brought to a pH of 7.0–7.5 by the addition of 400 lbs. of 85% formic acid, after which 10 lbs. of an ammonium sulfonate emulsifier, 8 lbs. of a blue dye and 10 lbs. of a suitable fragrance solution were stirred in.

EXAMPLE 3

600 lbs. of water has added thereto 1200 lbs. of a 26° Be. ammonium hydroxide. 1000 lbs. of cupric sulfate pentahydrate is then slowly added, with stirring, to the dilute ammonium hydroxide. Thereafter 100 lbs. of sodium chlorite was dissolved therein. The solution is then brought to pH of 7.5–8.0 by the addition of 300 lbs. of glacial acetic acid after which 10 lbs. of an ammonium sulfonate emulsifier and 10 lbs. of fragrance were stirred in. The resultant composition was added to a chemical toilet in the amount of about 1 pint per 2.5 gallons of water in a closed toilet system. The toilet was left in use for about 60 days at which time sufficient deterioration to produce odor had still not occurred.

EXAMPLE 4

600 lbs. of water has added thereto 600 lbs. of 26° Be. ammonium hydroxide and 600 lbs. of monoethanolamine. 1000 lbs. of cupric sulfate pentahydrate is then slowly added with stirring to the alkaline liquid. Thereafter 200 lbs. of sodium nitrate was dissolved therein. The solution is then brought to a pH of 7.5–8.0 by the addition of 450 lbs. of glacial acetic acid after which 10 lbs. of an ammonium sulfonate emulsifier and 10 lbs. of a commercial fragrance were stirred in.

Having now thus fully described and illustrated the nature of the invention what is desired to be secured by Letters Patent is:

1. An aqueous odor control composition for closed system chemical toilets comprising water, an admixture of zinc sulfate and zinc nitrate, and sufficient ammonium hydroxide to convert all of the zinc to the water soluble stoichiometric ammonia complex and to maintain a pH in the solution of at least about 10.5, adding sodium nitrate as an oxidizing agent, together with sufficient acetic acid to attain an aqueous solution having a pH of between about 7.0 and about 7.5.

2. An aqueous odor control composition for closed system chemical toilets comprising an admixture of water, zinc acetate, zinc nitrate, and sufficient ammonium hydroxide to convert all of the zinc contained therein to the water soluble stoichiometric ammonia complex and to maintain a pH in the solution of at least about 10.5, adding sodium nitrate as an oxidizing agent thereto, together with sufficient formic acid to attain an aqueous solution having a pH of between about 7.0 and about 7.5.

3. An aqueous odor control composition for closed system chemical toilets comprising an admixture of water, cupric sulfate and at least sufficient ammonium hydroxide to convert all of the copper contained therein to the water soluble stoichiometric ammonia complex and to maintain a pH in the solution of at least about 10.5, adding sodium chlorite as an oxidizing agent, together with sufficient glacial acetic acid to attain an aqueous solution having a pH of between about 7.5 and about 8.0.

4. An aqueous odor control composition for closed system chemical toilets comprising an admixture of water, cupric sulfate and a mixture of ammonium hydroxide and monoethanolamine in sufficient amount to convert all of the copper contained therein to the water soluble stoichiometric ammonia-amine complex and to maintain a pH in the solution of at least about 10.5, adding thereto, and dissolving therein, sodium nitrate and thereafter adding sufficient glacial acetic acid to attain an aqueous solution having a pH of between about 7.5 and about 8.0.

5. An aqueous odor control composition comprising water, admixed with water soluble transition metal salt whose metal is selected from the group consisting of zinc, copper, nickel, manganese, zirconium and chromium and whose anion is selected from the group consisting of chloride, bromide, sulfate, nitrate, acetate, trichloroacetate, formate, and citrate, and at least sufficient ammonium hydroxide or aqueous amine solution whose amine is selected from the group consisting of monoethanolamine, triethanolamine, dimethyl ethanolamine and diethylene triamine, to convert all of the transition metal contained therein to the water soluble stoichiometric complex and to maintain a pH in the solution of at least about 10.5 and thereafter adding to the so-formed solution sufficient weak organic mono- or dicarboxylic acid or anhydride thereof to obtain a solution having a pH of between about 6.5 and about 8.0.

6. The composition of claim 5 wherein an alkali metal salt whose anion is selected from the group consisting of permanganate, nitrate, chlorite and persulfate is added as an oxidizing agent.

7. The composition of claim 5 wherein the weak organic carboxylic acid or anhydride thereof is selected from the group consisting of citric, formic, acetic, propionic, butyric, phthalic, oxalic, malonic, benzoic, succinic, glutaric and adipic.

8. The composition of claim 7 wherein an alkali metal salt whose anion is selected from the group consisting of permanganate, nitrate, chlorite and persulfate is added as an oxidizing agent.

9. The composition of claim 5 wherein the anion of the transition metal is selected from the group consisting of chloride, bromide, sulfate, nitrate, acetate, trichloroacetate, formate and citrate, wherein the weak organic carboxylic acid or anhydride thereof is selected from the group consisting of citric, formic, acetic, propionic, butyric, phthalic, oxalic, malonic, benzoic, succinic, glutaric and adipic, and wherein an alkali metal salt whose anion is selected from the group consisting of permanganate, nitrate, chlorite and persulfate is added as an oxidizing agent.

* * * * *